US00PP25779P3

(12) United States Plant Patent
Nielsen

(10) Patent No.: US PP25,779 P3
(45) Date of Patent: Aug. 4, 2015

(54) *DAHLIA* PLANT NAMED 'DAFEMOGTYVE'

(50) Latin Name: *Dahlia Cav.*
Varietal Denomination: DAFEMOGTYVE

(71) Applicant: DALINA GENETICS A/S, Odense N (DK)

(72) Inventor: Rune Harboe Nielsen, Grönnegyden (DK)

(73) Assignee: Dalina Genetics A/S, Odense N (DK)

( * ) Notice: Subject to any disclaimer, the term of this patent is extended or adjusted under 35 U.S.C. 154(b) by 116 days.

(21) Appl. No.: 13/987,812

(22) Filed: Sep. 6, 2013

(65) Prior Publication Data

US 2015/0074862 P1 Mar. 12, 2015

(51) Int. Cl.
*A01H 5/02* (2006.01)

(52) U.S. Cl.
USPC ..... Plt./321

(58) Field of Classification Search
USPC ..... Plt./321
See application file for complete search history.

(56) References Cited

PUBLICATIONS

Plant Variety Protection for Dahlia 'DAFEMOGTYVE', European—Community Plant Variety Office (CPVO) Application No. 2012/128, filed May 22, 2012.*
Printout of application information from Community Plant Variety Office (CPVO) website for corresponding CPVO application No. 2012/1128 filed May 22, 2012. (1 page) (http://www.cpvoextranet.cpvo.europa.eu).

* cited by examiner

*Primary Examiner* — Anne Grunberg
(74) *Attorney, Agent, or Firm* — Foley & Lardner LLP

(57) ABSTRACT

A new distinct cultivar of *Dahlia* plant named 'DAFEMOGTYVE', characterized by its upright to spreading shape, with stiff and strong lateral stems and thick (mostly single but few with 2-3 leaflets) leaves; color of mature leaves are RHS Yellow-Green 147A (but darker) on the upper side, RHS Greyed-Green 191A on the underside; compound leaves 10-15 cm (4-5.9 in) in length, and 6-11 cm (2.4-4.3 in) in width. The more common single leaves are 5-15 cm (2-5.9 in) in length and 3-8 cm (1.2-3.1 in) in width; composite flower heads, 8-9 cm (3.1-3.5 in) in diameter, and a large number of RHS Red 45B ray florets (about 90-110).

8 Drawing Sheets

Latin name of the genus and species of the claimed plant: *Dahlia Cav.*

Variety denomination: 'DAFEMOGTYVE'.

BACKGROUND OF THE INVENTION

The present invention relates to a new and distinct cultivar of *Dahlia* plant (breeders reference: 6996B), botanically known as *Dahlia Cav.*, of the Compositae (Asteraceae) family. Hereinafter referred to by the cultivar name 'DAFEMOGTYVE'.

The new *Dahlia* cultivar is a product of a planned breeding program conducted by the inventor, Rune Nielsen, in Stige, Denmark. The objective of the breeding program is to develop a new *Dahlia* cultivar with an upright, strong and healthy growth habit, and with good garden performance; fully double flowers (composite flower heads with many ray florets) with an attractive inflorescence color.

The new *Dahlia* cultivar originated from a cross, made in a controlled breeding program by the inventor in 2009, in Stige, Denmark. The female or seed parent is a red *Dahlia* cultivar designated 4416G (unpatented in the US). The male or pollen parent is a Red colored *Dahlia* variety designated 'HAWAI' (CPVO grant no. 11446, unpatented in the US).

Asexual reproduction of the new *Dahlia* cultivar by terminal cuttings was first performed in November, 2010 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAFEMOGTYVE', which in combination distinguish this *Dahlia* as a new and distinct cultivar:

1. Cultivar with upright to spreading shape;
2. Cultivar with stiff and strong lateral stems and thick, mostly single leaves, but few with 2-4 leaflets. Color of mature leaves are RHS Yellow-Green 147A, but darker (upper side), RHS Greyed-Green 191A (underside);
3. Compound leaves 10-15 cm (4-5.9 in) in length, and 6-11 cm (2.4-4.3 in) in width. The more common single are leaves 5-15 cm (2-5.9 in) in length and 3-8 cm (1.2-3.1 in) in width;
4. Composite flower heads, 8-9 cm (3.1-3.5 in) in diameter, with a large number of ray florets (about 90-110); and
5. Ray florets which are RHS Red 45B on the upper side.

Plants of the new *Dahlia* 'DAFEMOGTYVE' differ from plants of the parent; 'HAWAI' (CPVO grant no. 11446, unpatented in the US), in the traits described in Table 1.
(The unpatented female parent 4416G is no longer available for comparison).

TABLE 1

| Trait | Comparison with Parent Variety: New Cultivar 'DAFEMOGTYVE' | Comparison, male parent 'HAWAI' CPVO grant no. 11446 |
|---|---|---|
| Plant Size | | |
| Height: | About 17-18 cm (6.7-7 in). | About 17-18 cm (6.7-7 in). |
| Diameter: | About 26-28 cm (10.2-11 in). | About 26-28 cm (10.2-11 in). |
| Overall Plant Shape: | Upright to spreading, with basal branching. Inflorescences in composite heads. | Cylindrical, upright to slightly spreading, with basal branching. Inflorescences in composite heads. |
| Basal branches (including flowers) | | |
| Length: | About 18-20 cm (7-7.9 in). | About 17-19 cm (6.7-7.5 in). |
| Diameter: | About 8-9 mm (0.31-0.35 in). | About 8-9 mm (0.31-0.35 in). |
| Strength: | Stiff and strong. | Stiff and strong. |
| Color: | RHS Yellow-Green 146A. | RHS Yellow-Green 146B. |
| Leaves Colour mature | | |
| upper side: | RHS Yellow-Green 147A (but darker). | RHS Yellow-Green 147A (but darker). |
| Underside: | RHS Grayed-Green 191A | RHS Grayed-Green 191. |
| Peduncle Diameter: | About 3-4 mm (0.12-0.16 in). | About 3-4 mm (0.12-0.16 in). |
| Color of ray florets Upper side: | RHS Red 45B. | RHS Red 45B. |
| Ray florets Quantity per Inflorescence head: | 90-100. | 55-65. |

Of the many commercial cultivars known to the present inventor, the most similar in comparison to the new *Dahlia* 'DAFEMOGTYVE' is the *Dahlia* cultivar 'HAWAI' (CPVO grant no. 11446, unpatented in the US), in the characteristics described in Table 2:

TABLE 2

| Trait | Comparison with Parent Variety: New Cultivar 'DAFEMOGTYVE' | Comparison, male parent 'HAWAI' CPVO grant no. 11446 |
|---|---|---|
| Plant Size | | |
| Height: | About 17-18 cm (6.7-7 in). | About 17-18 cm (6.7-7 in). |
| Diameter: | About 26-28 cm (10.2-11 in). | About 26-28 cm (10.2-11 in). |
| Overall Plant Shape: | Upright to spreading, with basal branching. Inflorescences in composite heads. | Cylindrical, upright to slightly spreading, with basal branching. Inflorescences in composite heads. |
| Basal branches (including flowers) | | |
| Length: | About 18-20 cm (7-7.9 in). | About 17-19 cm (6.7-7.5 in). |
| Diameter: | About 8-9 mm (0.31-0.35 in). | About 8-9 mm (0.31-0.35 in). |
| Strength: | Stiff and strong. | Stiff and strong. |

TABLE 2-continued

| Trait | Comparison with Parent Variety: New Cultivar 'DAFEMOGTYVE' | Comparison, male parent 'HAWAI' CPVO grant no. 11446 |
|---|---|---|
| Color: | RHS Yellow-Green 146A. | RHS Yellow-Green 146B. |
| Leaves Colour mature | | |
| upper side: | RHS Yellow-Green 147A (but darker). | RHS Yellow-Green 147A (but darker). |
| Underside: | RHS Grayed-Green 191A | RHS Grayed-Green 191. |
| Peduncle Diameter: | About 3-4 mm (0.12-0.16 in). | About 3-4 mm (0.12-0.16 in). |
| Color of ray florets Upper side: | RHS Red 45B. | RHS Red 45B. |
| Ray florets Quantity per Inflorescence head: | 90-100. | 55-65. |

BRIEF DESCRIPTION OF THE PHOTOGRAPHS

The accompanying photographs illustrate the overall appearance of the new *Dahlia* 'DAFEMOGTYVE' showing the colors as true as is reasonably possible with colored reproductions of this type. Colors in the photographs may differ slightly from the color value cited in the detailed botanical description, which accurately describe the color of 'DAFEMOGTYVE'.

DETAILED BOTANICAL DESCRIPTION

Figure 1:
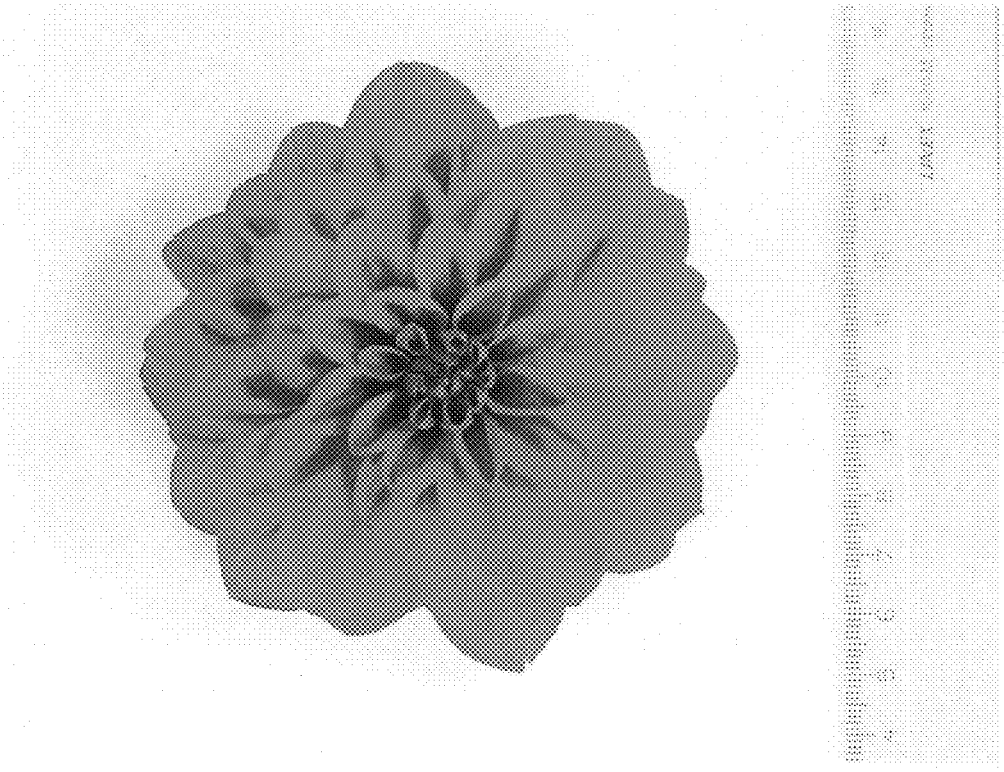
FIG. 1 shows a close-up view of the composite flower head from 'DAFEMOGTYVE'.
Figure 2:
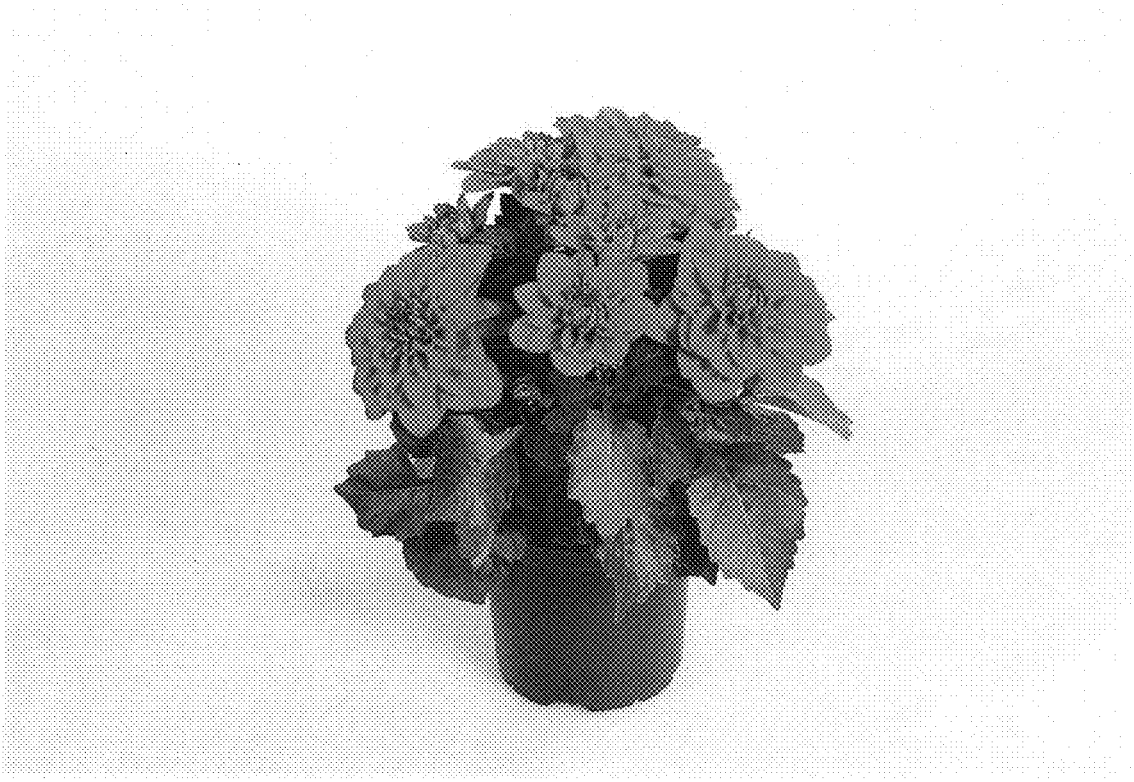
FIG. 2 shows a side view perspective of a typical flowering plant of 'DAFEMOGTYVE' in a 11 cm (4.3 in) pot, at 7 weeks of age after potting the young plant.
Figure 3:
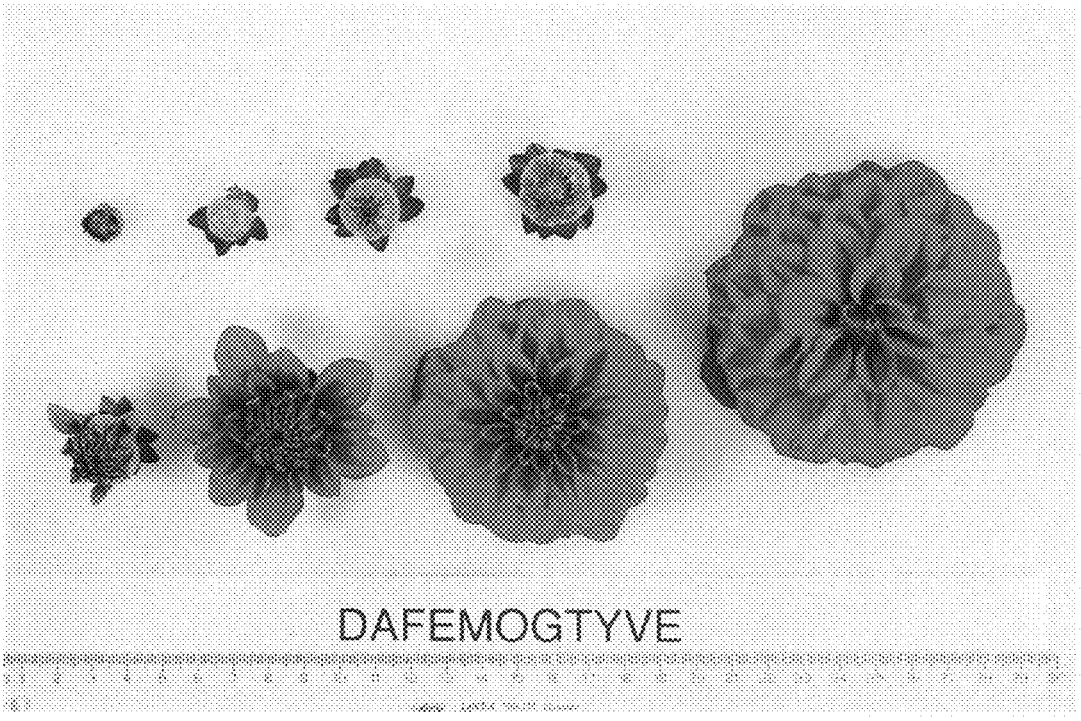
FIG. 3 shows a close-up view of different development stages of the composite flower head of 'DAFEMOGTYVE'.
Figure 4:
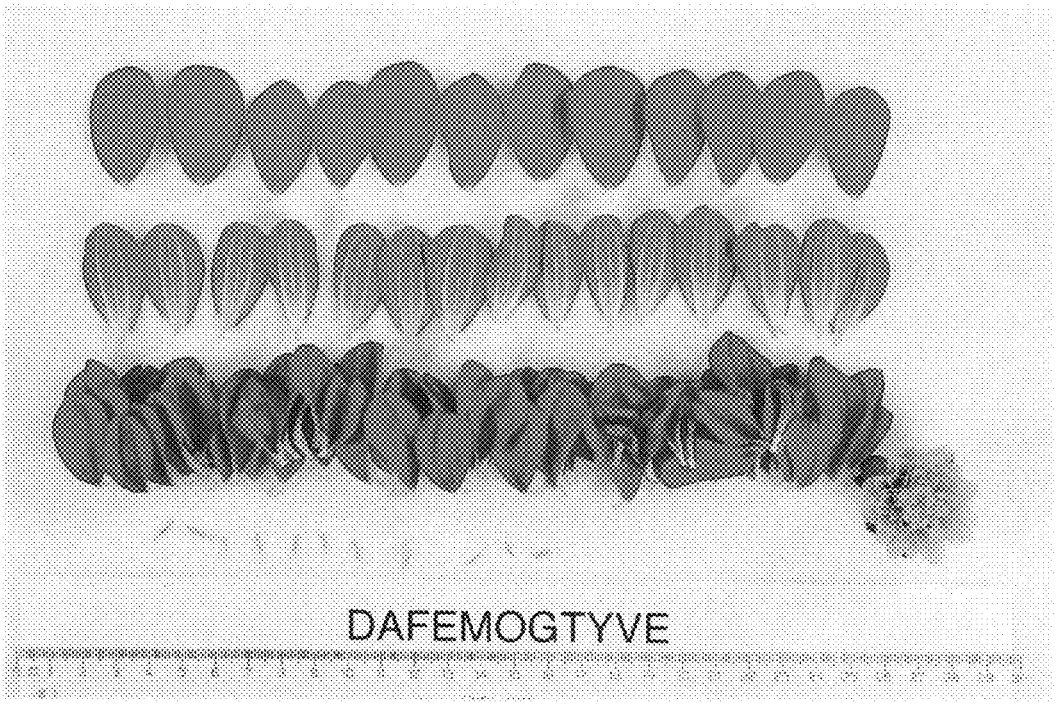
FIG. 4 shows a close-up view of the 90-110 ray florets from one composite flower head of 'DAFEMOGTYVE'
Figure 5:
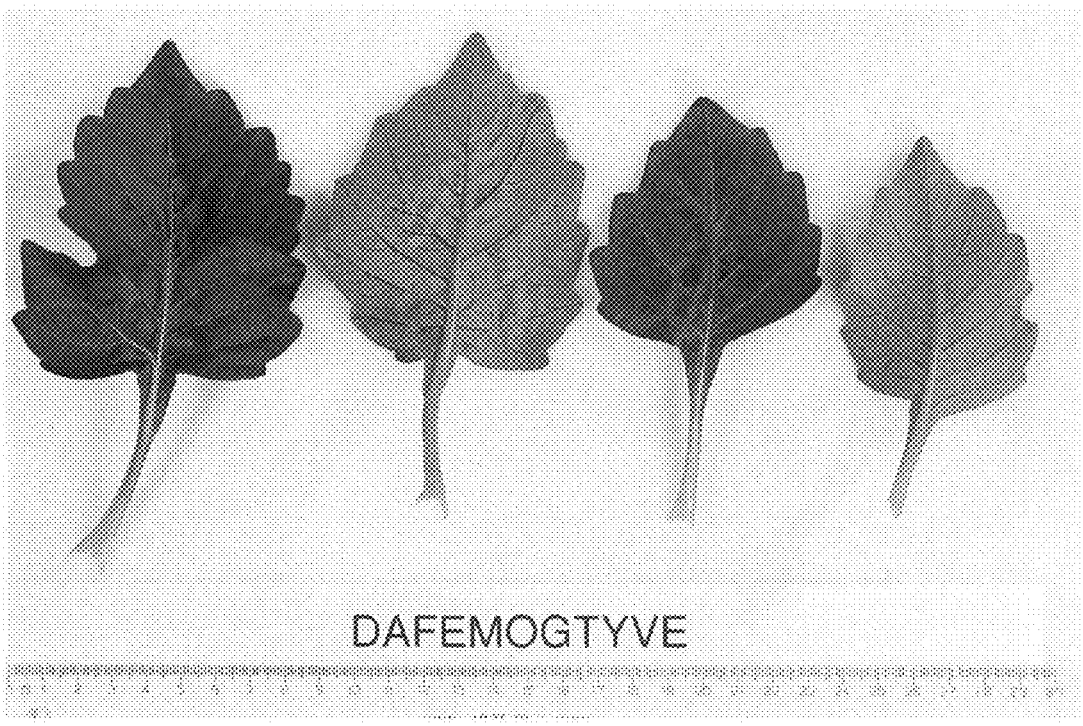
FIGS. 5, 6 and 7 show close-up views of the different single and compound leaf sizes of 'DAFEMOGTYVE'.
Figure 6:
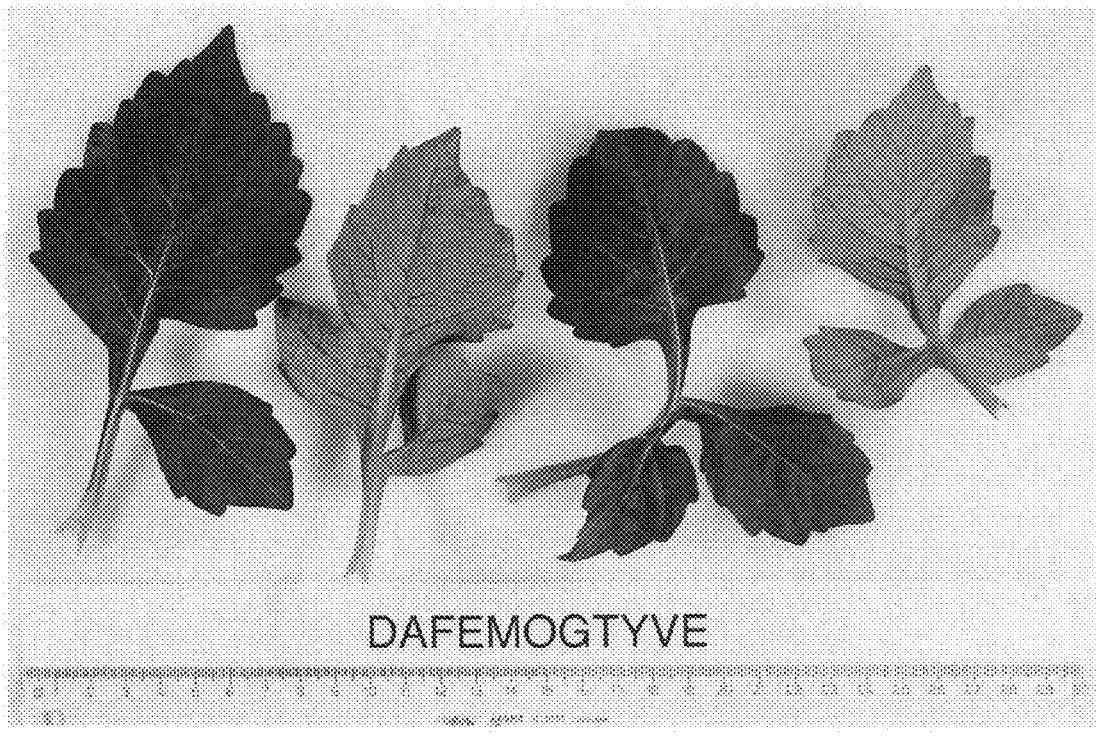
Figure 7:
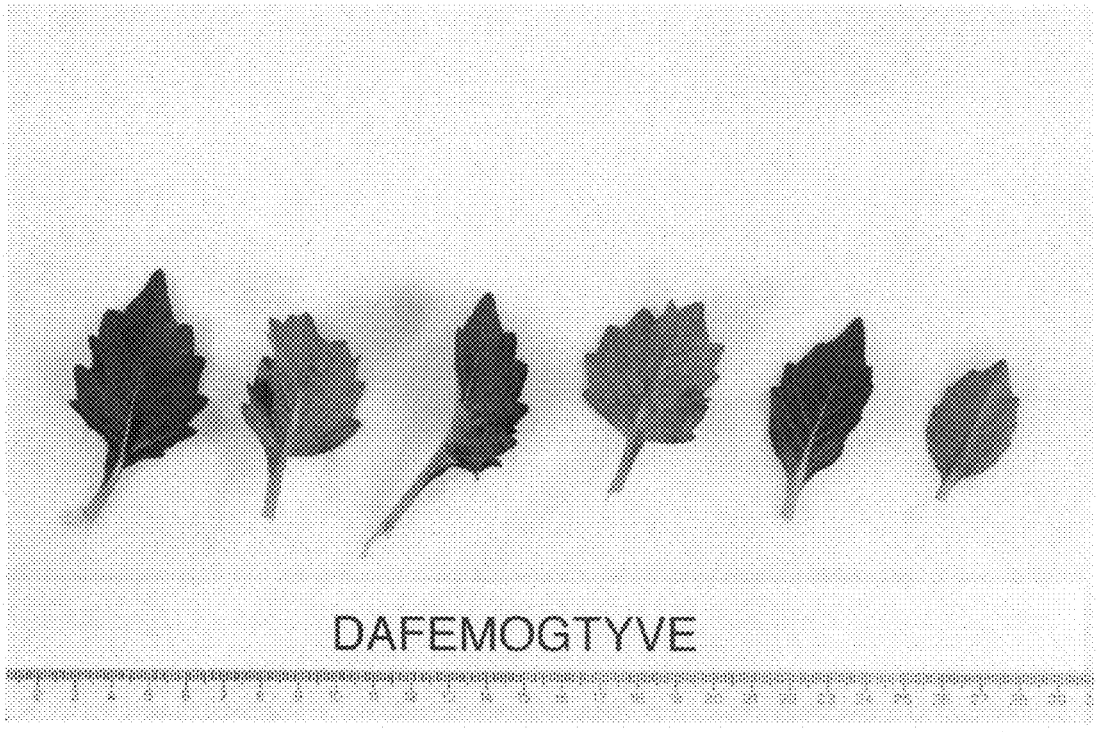
Figure 8:
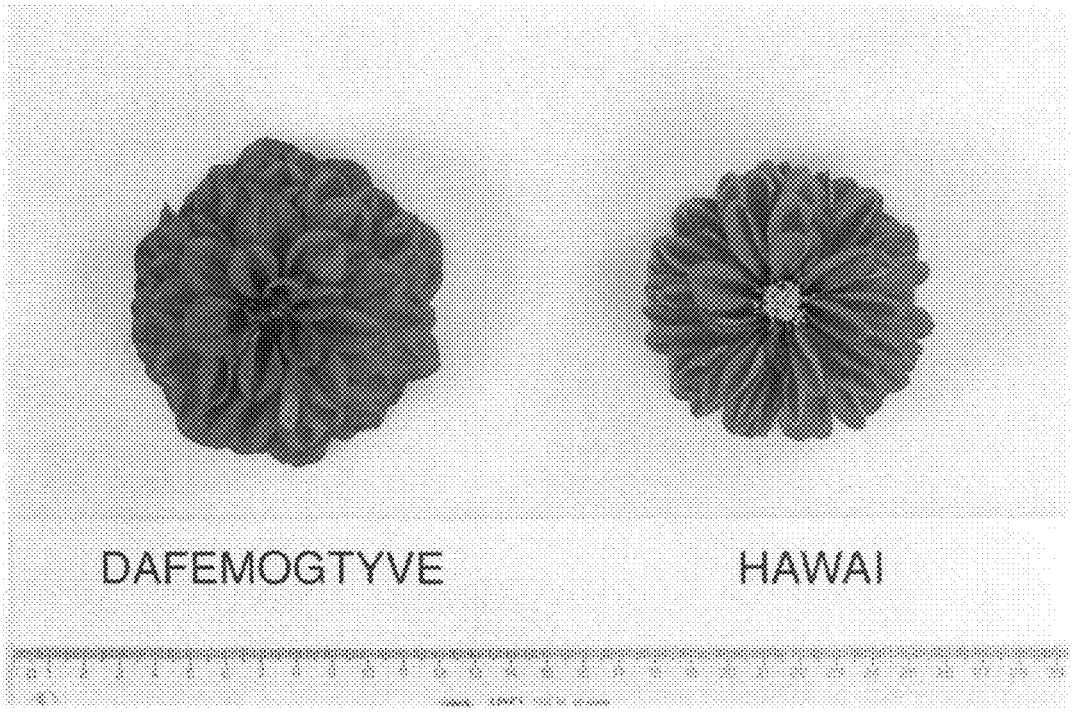
FIG. 8 shows a comparison between 'HAWAI' and 'DAFEMOGTYVE'.

The new *Dahlia* 'DAFEMOGTYVE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'DAFEMOGTYVE' as grown in a protected environment in a glass, greenhouse in Fyn, Odense, Denmark, under conditions which closely approximate those generally used in commercial practice. During propagation, conducted in a glasshouse, vegetative cuttings were planted in small propagation pots with peat as substrate, and then placed in a plastic tunnel averaging about 21° C. (69.8° F.) and received photoperiodic treatments of 18 hours. Supplementary light was given when natural light fell below 3000-4000 Lux. Rooting occurred about 9-12 days after planting. In third week after sticking the cutting, the young plants were potted in a 19 cm pot in a glass-covered greenhouse, maintained at 18-22° C. (64.4-71.6° F.) during the day (warmer during sunny days), and at 17-19° C. (62.6-66.2° F.) during the night. Photoperiodic treatments were continued at 18 hours, and supplementary light was given when natural light fell below 3000-4000 Lux. Irrigation was done with water. The EC (μS/m) measured in the soil was maintained between 2.0 to 3.0. One week after potting, the first growth regulation was given: a spray with 85% daminozide, 0.2%, 40-100 ml/m$^2$. During the production time, 9 additional sprayings were given with 85% daminozide, 0.2%, 40-100 ml/m2.

Color references are made to The Royal Horticultural Society Colour Chart (R.H.S.), 2001 edition, except where general colors of ordinary significance are used. Color values were taken under June daylight conditions at approximately 12:00 PM and 2:00 PM in Fyn, Odense, Denmark. The age of the 'DAFEMOGTYVE' plants described is 10 weeks (including propagation time).

Classification:

*Botanical.*—*Dahlia Cav.*

Parentage:

*Female or seed parent.*—*Dahlia* variety designated 4416G (Unpatented).

*Male or pollen parent.*—*Dahlia* variety designated 'HAWAI' (CPVO grant no. 11446, unpatented in the US).

Propagation:

*Type.*—Vegetative terminate cuttings.

*Time and temperature to initiate roots.*—About 9-12 days at 21° C. (69.8° F.) in tunnels or flat covered in a greenhouse.

*Time and temperature to produce a rooted young plant.*—About 21 days at 21° C. (69.8° F.) during rooting phase, followed by 18° C. (64.4° F.).

*Rooting habit.*—Fine, fibrous; Color of root: RHS Yellow-white 158A.

*Tuber development.*—Plants might develop tubers in late fall when planted outside.

Plant description:

*General appearance and form.*—Upright to spreading, with basal branching. Inflorescences in composite heads.

*Growth rate.*—Growing about 1 to 3 cm per week during production period.

*Plant height* (*from soil level to top of plant plane*).—About 17-18 cm (6.7-7 in).

*Plant width* (*spread*).—About 26-28 cm (10.2-11 in).

*Crop time to produce a mature flowering plant.*—It requires 3 weeks to produce a young plant in a 35 mm (1.4 in) propagation plug. After potting, 8 to 10 weeks are required to produce finished flowering plants in 11 cm (4.3 in) pots.

Stem: Plants have been pinched a present soil level, so branches might be considered the stems.

Branches:

*Branching habit.*—Basal branching (increased because of the pinching); few lateral branches.

*Number of basal branches per plant.*—About 3-5 (when pinched above 3 pair of leaves).

*Length* (*including flowers*).—About 17-18 cm (6.7-7 in).

*Diameter.*—About 6-8 mm (0.24-0.31 in).

*Strength.*—Stiff and strong.

*Aspect.*—Upright to slightly spreading.

*Texture.*—Smooth and glabrous.

*Color.*—Mature: RHS Yellow-Green 146B. Immature: RHS Yellow-Green 146B.

*Internodes length.*—About 10-15 mm (0.39-0.59 in).

*Internodes color.*—RHS Yellow-Green 146B.

Foliage description:

*Type.*—Lower leaves: Single. Middle leaves: Single and a few compound, 2-4 lobed. Upper leaves: Single.

*Number of leaves per branch.*—About 8-10 per branch.

*Color of leaves* (*leaves and leaflets*).—Color of upper side (mature) RHS Yellow-Green 147A (but darker). Color of underside (mature) RHS Grayed-Green 191A. Color of upper side (immature) RHS Green 137A. Color of underside (immature) RHS Green 137B.

*Venation* (*leaves and leaflets*).—Pattern: Pinnate. Color of upper side: RHS Yellow-Green 146A. Color of underside: RHS Yellow-Green 146B.

Compound leaves:

*Number of leaflets per compound leaf.*—2-3.

*Length of compound leaf.*—10-15 cm (4-5.9 in).

*Width of compound leaf.*—6-11 cm (2.4-4.3 in).

*Petiole of compound leaves.*—Shape: Semi circular, with deep furrow on adaxial side. Length: 3-5 cm (1.2-2.0 in). Diameter: 3-6 mm (0.12-0.24 in). Texture: Smooth and glabrous. Color Upper side along furrow: RHS Yellow-Green 146A. Underside: RHS Yellow-Green 146B.

*Leaflets of compound leaf.*—Terminal leaflet quantity: 1. Terminal leaflet length: 6-8 cm (2.4-3.1 in). Terminal leaflet width: 3-6 cm (1.2-2.4 in). Terminal leaflet shape: Ovate. Terminal leaflet shape at apex: Acuminate. Terminal leaflet shape at base: Rounded to cordate. Terminal leaflet margin: Dentate. Terminal leaflet texture (both sides): Rugose. Rachis length: 0-20 mm (0-0.8 in). Rachis Diameter: 3-5 mm (0.12-0.2 in). Rachis color Upper side along furrow: RHS Yellow-Green 146A. Underside: RHS Yellow-Green 146B. Lateral leaflet quantity: 1-3. Lateral leaflet length: 3-5 cm (1.2-2 in). Lateral leaflet width: 1.5-3 cm (0.6-1.2 in). Lateral leaflet overall shape: Ovate. Lateral leaflet shape at apex: Acuminate (mostly asymmetric). Lateral leaflet shape at base: Attenuate to rounded (not always symmetric). Lateral leaflet margin: Dentate. Lateral leaflet texture (both sides): Rugose.

Simple leaves:

*Simple leaves overall shape.*—Ovate.

*Simple leaves shape at apex.*—Acuminate.

*Simple leaves shape at base.*—Cordate to rounded.

*Simple leaves length.*—5-15 cm (2-5.9 in).

*Simple leaves width.*—3-8 cm (1.2-3.1 in).

*Simple leaves margin.*—Dentate.

*Simple leaves texture.*—Rugose.

*Petiole shape.*—Semi circular, with deep furrow on adaxial side.

*Petiole length.*—1-6 cm (0.4-2.4 in).

*Petiole diameter.*—3-6 mm (0.12-0.24 in).

*Petiole texture.*—Smooth and glabrous.

*Petiole color.*—RHS Yellow-Green 146B. Upper side along furrow: RHS Yellow-Green 146A. Underside: RHS Yellow-Green 146B.

Inflorescence description:

*Natural flowering season.*—Grown outside as a bedding plant, flowering occurs continuously during growing season from spring to autumn/(In Denmark, from June to beginning of October). Plants can be brought to flower anytime when grown under the recommended greenhouse conditions.

*Time to flower.*—40 to 50 days from potting a young plant until flowering.

*Inflorescence longevity on the plant.*—Inflorescence will maintain good color and substance for about 4-8 days; however, the longevity of individual inflorescence is highly dependent on temperature and light conditions. Inflorescence persistent.

*Type.*—Composite flower heads.

*Arrangement and shape.*—Persistent, single, composite inflorescences from leaf axils. Disc and ray florets arranged acropetally in a composite flower head. Upright, slightly spreading. Terminal young flower head/buds initially 0-20°. Buds from axillary shoots; 20-90°. When flower opens 10-30°.

*Quantity of inflorescences heads.*—Freely flowering; about 16 buds and open inflorescences per plant.

*Fragrance.*—None.

*Bud* (*inflorescences head*).—Rate of opening (from showing color to fully open): 4-8 days. The rate of opening is highly dependent on temperature and light conditions. Length: About 10-12 mm (0.39-0.47 in). Diameter: About 14-16 mm (0.55-0.63 in). Shape: Flat globular. Texture: Glabrous, shining. Color: RHS Yellow-Green 144B, tip of phyllaries are RHS Grayed-Orange 163A.

*Peduncle.*—From both terminate and axillary shoots. Length: About 4-8 cm (1.6-3.1 in). Diameter: About 3-4 mm (0.12-0.16 in). Angle: About 0-20° from vertical. Strength: Stiff and strong. Texture: Glabrous and slightly glaucous. Color (mature): RHS Yellow-Green 146B, some parts RHS Brown between N200A and N 200B. Color (immature): RHS Yellow-Green 146A.

*Receptacle.*—Height: About 3 mm (0.12 in). Diameter: About 6-8 mm (0.24-0.31 in). Color: RHS Yellow-Green 146A.

*Inflorescence head.*—Depth (height): About 4-5 cm (1.6-2 in). Diameter: About 8-9 cm (3.1-3.5 in).

*Disc diameter.*—About 7-9 mm (0.28-0.35 in).

*Ray florets.*—Arrangement: Imbricate, in about 10-12 whorls of ray florets, each with approx. 10 florets to equal a total of about 90-110 ray florets per flower head, depending on light and temperature conditions. Quantity per Inflorescence head: 90-110. Length: 35-45 mm (1.4-1.8 in). Widths: 22-26 mm (0.9-1 in). Overall shape: Obovate. Apex shape: Rounded. Base shape: Acuminate, slightly fused. Margin: Entire, with 1-3 very small (1 mm) teeth at the apex. Texture: Glabrous (upper side and underside). Color when opening Fused ray floret starting to show color: RHS Red 45A. Color when fully opened Color upper side: RHS Red 45B. Color underside: RHS Red 45 and RHS Green-Yellow 1D on the first 10 mm near base, developing into thin stripes in the full length of the ray floret.

*Disc florets.*—Arrangement: 35-45 yellow-orange disc florets arranged in the center of inflorescence head. Appearance: Quantity per Inflorescence head: 35-45. Length: 11-12 mm (0.43-0.47 in). Diameter: 2 mm (0.08 in). Overall shape: Tubular. Apex shape: Star with 5 triangular tips. Base shape: Fused to tube. Color RHS Yellow-Orange 17A, RHS Yellow-Green 145D near base.

*Phyllary.*—Arrangement: One subtending each floret. Quantity: 125-155. Length: 15-18 mm (0.6-0.7 in). Width: 7-10 mm (0.28-0.39 in). Overall shape: Rounded. Shape at apex: Acute with rounded tip. Shape at base: Fused. Margin: Entire. Color: Mature: RHS Yellow-Green 151A. RHS Yellow-Green 144A on underside of the 8-10 phyllaries in the outer whorl. Immature: RHS Yellow-Green 151A (both sides).

*Bracts.*—Arrangement and appearance: Reflexed, involucral bracts. Quantity: 7-9. Length: 12-16 mm (0.47-0.62 in). Width: 6-10 mm (0.24-0.39 in). Overall shape: Subulate. Apex shape: Acute. Base shape: Sessile. Margin: Entire. Texture: Glabrous. Colour mature Upper side: RHS Green 137A. Underside: RHS Green 137B. Colour immature Upper side: RHS Green 137A. Underside: RHS Green 137B.

Reproductive organs:

*Androecium.*—Location: Disc florets only. Stamen number: 5, fused into synandrous tube around style. Stamen length: About 8 mm (0.31 in). Anther shape: Tubular. Anther length: About 4-5 mm (0.16-0.2 in). Pollen amount: Some. Pollen color: RHS Orange N25C.

*Gynoecium.*—Location: Ray and disc florets (Gynoecium at ray florets is very poorly developed). Quantity: 1. Pistil length: About 12 mm (0.47 in). Stigma shape: Bifurcate. Stigma length: About 4 mm (0.16 in). Stigma color: RHS Orange N25D. Style length: About 8 mm (0.31 in). Style color: RHS Yellow 2C. Ovary color: RHS Yellow 2D.

Seed/fruit: Seed and fruit production has not been observed.

Disease/pest resistance: Resistance to pathogens and pests common to *Dahlia* has not been observed.

Disease/pest susceptibility: Susceptibility to pathogens and pests common to *Dahlia* has not been observed.

Temperature tolerance: Plants of the new *Dahlia* have exhibited good tolerance to rain, wind and drought; however, flowering may cease during hot periods (temperatures above 25° C./77° F.). Low temperature tolerance to 1° C./33.8° F.

Growth regulators: Daminozide (85% water soluble dryconcentrate formulation).

What is claimed is:

1. A new and distinct cultivar of *Dahlia* plant named 'DAFEMOGTYVE', as illustrated and described herein.

* * * * *